(12) United States Patent
Cole

(10) Patent No.: US 8,218,215 B2
(45) Date of Patent: Jul. 10, 2012

(54) TRANSDUCER-MIRROR STRUCTURE

(75) Inventor: Barrett E. Cole, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 506 days.

(21) Appl. No.: 12/144,382

(22) Filed: Jun. 23, 2008

(65) Prior Publication Data
US 2009/0316245 A1   Dec. 24, 2009

(51) Int. Cl.
G02B 26/08 (2006.01)
G02B 26/10 (2006.01)

(52) U.S. Cl. .................. 359/200.2; 359/221.2

(58) Field of Classification Search ............... 359/198.1, 359/200.1–200.3, 221.2–221.3
See application file for complete search history.

(56) References Cited

U.S. PATENT DOCUMENTS

| 5,311,280 | A | 5/1994 | Koper et al. |
| 5,832,017 | A | 11/1998 | Ramdani et al. |
| 5,912,740 | A | 6/1999 | Zare et al. |
| 7,145,165 | B2 | 12/2006 | Cox et al. |
| 7,807,061 | B2 * | 10/2010 | Wado et al. ............ 216/2 |
| 2002/0131679 | A1 * | 9/2002 | Nasiri ................. 385/18 |
| 2005/0035699 | A1 * | 2/2005 | Tsai .................. 313/110 |
| 2005/0046980 | A1 * | 3/2005 | Mizuno et al. ........ 359/877 |
| 2007/0139752 | A1 * | 6/2007 | Bernstein et al. ...... 359/224 |

* cited by examiner

*Primary Examiner* — Jade R. Chwasz
(74) *Attorney, Agent, or Firm* — Seager Tufte Wickhem LLC

(57) ABSTRACT

An approach for obtaining a transducer mirror structure made from silicon. The structure may have a center portion and a perimeter portion that have an attachment between them which is made flexible after certain etching between the two portions. The attachment may be a web of links or legs. A force applied to the center portion at one end of the structure may cause the center portion to move relative to the perimeter portion. A piezo electric transducer or actuator may be attached to apply the force. An oxide layer, a thin layer of silicon and a mirror may be formed on the other end of the structure. The web of links or legs between the center and the perimeter portions may be established with an RIE etch of gaps through the structure to the oxide layer and an undercutting of the gaps with a KOH etch.

8 Claims, 14 Drawing Sheets

TRANSDUCER-MIRROR STRUCTURE

BACKGROUND

The invention pertains to cavities and particularly to cavity mirrors. More particularly, the invention pertains to transducer mirrors.

SUMMARY

The invention is a silicon-based transducer-mirror structure. The transducer structure may have two portions made by etching a piece of silicon. One portion may be for holding a mirror and the other portion may be for mounting to another structure such as, for example, a cavity. An actuator may be attached to the transducer-mirror structure to cause movement of one portion relative to the other portion of the structure.

DESCRIPTION

Figure 14:
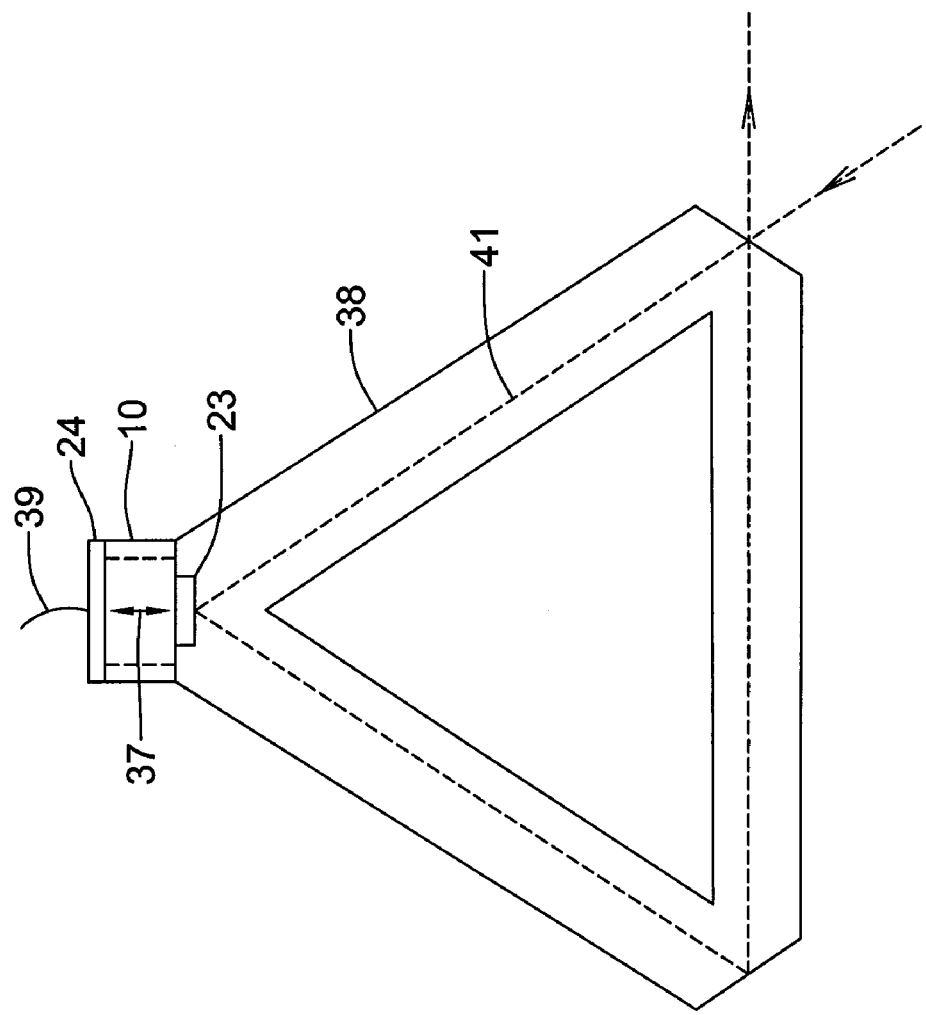
FIG. 14 is a diagram of the transducer mirror structure attached to another structure.

It is highly desirable to tune optical cavity mirrors such as those used in cavity ring down spectroscopy so that the path length in the cavity is an integral number of wavelengths, such as in light path 41 in structure 38 shown in FIG. 14. This may be done for an optical gyro by machining a mirror place and a read web structure out of glass. This structure may be expensive to make from glass, but it can provide parallelogram motion for keeping the mirror area and a respective mirror situated on the area facing one direction and being in line with an axis during the motion. The axis may be a normal or perpendicular relative to the surface of the area. Such structure may be made from silicon and have these motion properties. The structure may be designed to have other motion properties. The invention includes this structure made from silicon or like material. This structure may be used to adjust a light path length in a cavity.

A cavity ring down spectroscopy or system (CRDS) may be described in U.S. patent application Ser. No. 12/137,007, filed Jun. 11, 2008; U.S. patent application Ser. No. 11/770,648, filed Jun. 28, 2007; U.S. patent application Ser. No. 11/633,872, filed Dec. 4, 2006; and U.S. patent application Ser. No. 10/953,174, filed Sep. 28, 2004, now U.S. Pat. No. 7,145,165. U.S. patent application Ser. No. 12/137,007, filed Jun. 11, 2008; U.S. patent application Ser. No. 11/770,648, filed Jun. 28, 2007; U.S. patent application Ser. No. 11/633,872, filed Dec. 4, 2006; and U.S. patent application Ser. No. 10/953,174, filed Sep. 28, 2004, now U.S. Pat. No. 7,145,165, are hereby incorporated by reference.

The present device with similar qualities of a glass transducer mirror structure may be made out of silicon with appropriate processes. It may be a laterally translatable mirror structure. A combination of reactive ion etching and KOH etching may be used to define the legs or supporting links. A sacrificial layer such as that used on SOI wafer may be used to stop the etch on an SiO2 layer. This layer may later be removed or left as is. Thus, the front membrane may be the thickness of the SOI layer. The back web of legs or links may be formed out of a structure that is defined by a top silicon nitride pattern on the wafer which is later removed by chemical or plasma etching.

In other words, one might start with an SOI (silicon on insulator) wafer which has a Si layer on a thin oxide layer which in turn is on a thick Si layer. The front surface may be formed by etching spider legs "almost" all the way through the thick layer. The back legs which are on the side may be formed by etching up to the $SiO_2$ SOI etch stop.

The present device may be situated in a cavity block and optically sealed to the block. A piezo driver or other actuator may be mounted such that it pushes against the center part while the outside of the device forms a seal with the optically smooth cavity block surface at the mirror mount position.

The present silicon device may also be integrated with a block that is formed of silicon rather than glass. The potential for making smaller blocks at lower cost with low cost mirrors makes the CRDS more attractive to make for a number of applications.

Figure 1:
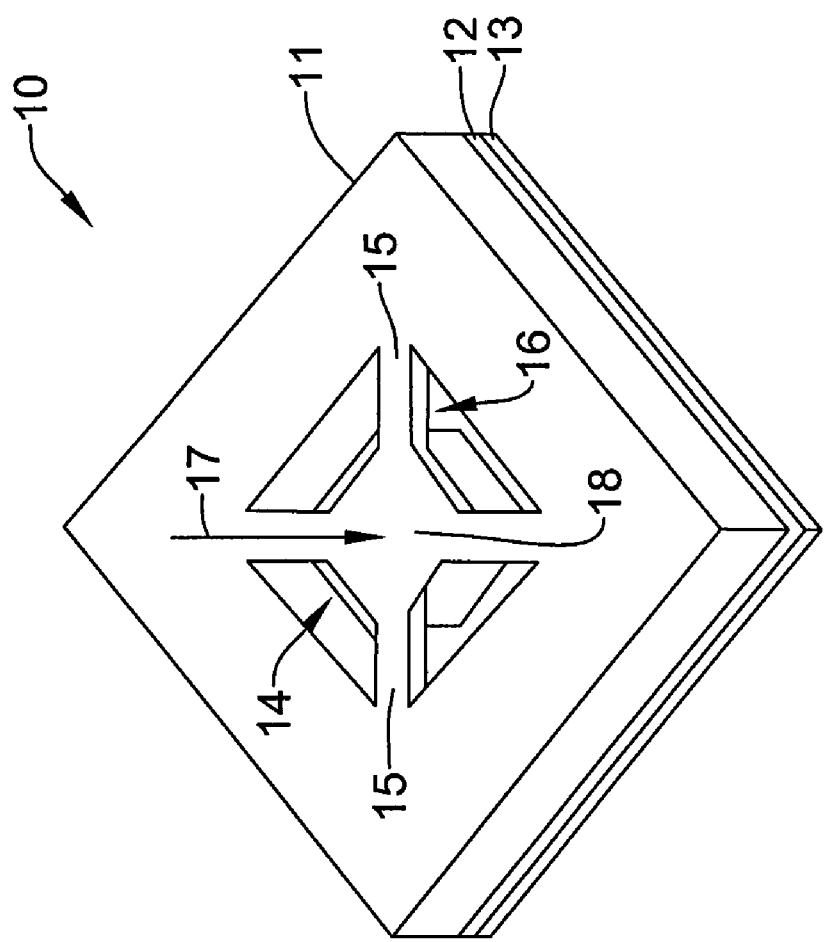
FIG. 1 is a diagram of a transducer mirror structure having a center portion for holding a mirror and a peripheral portion for mounting to another structure such as a cavity.

FIG. 1 is a diagram or insulator (SOI) cavity ring down system or sensor (CRDS) mirror structure 10. A layer 11 may be silicon on one side of an $SiO_2$ insulator 12. Also a silicon layer 13 may be on the other side of $SiO_2$ insulator layer 12. A mirror layer may be formed on layer 13. Layer 13 may have a thickness of, for instance, about 30 microns. The layers 11, 12 and 13 may be designed with various thicknesses as appropriate for a respective application of structure 10.

Layer 11 may be etched down in selected spots to the $SiO_2$ layer 12 with a deep RIE as shown with arrow 14. Also, a KOH etching approach may be used to etch under the legs 15 in that the etching causes an undercut as shown by arrow 16. RIE may etch or cut straight ahead whereas KOH tends to undercut. Legs 15 may of various sorts of shapes, so long as pressure on one side of the structure 10 moves a mirror on the other side of the structure along a straight or other designed optical path relative to structure 10.

The structure 10 may have a low RMS surface roughness. There may be a membrane or seal around the perimeter of the transducer-mirror structure 10 so that it may be hermetic when the structure 10 is inserted on or in an opening or installed as part of another structure such as, for instance, a cavity. Structure 10 may include layers 12 and 13 which hold and support the mirror.

Figure 6:
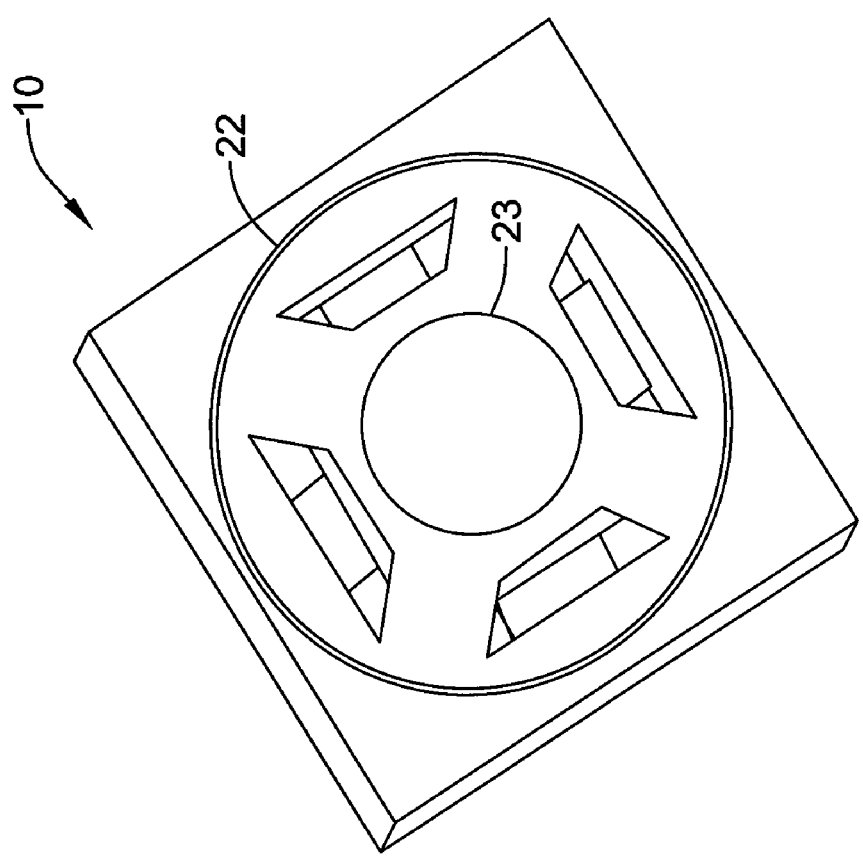
FIG. 6 is a diagram of the transducer mirror structure having a mirror formed on a surface of an inner portion of the structure.

A central portion of surface 13 on which the mirror is formed may be moved relative to the outside portion of structure 11 with a pressure 17 exerted against area 18. Such pressure 17 may be effected with a piezo electric actuator or other mechanism. The mirror on the external surface of layer 13 may be a ring laser gyro (RLG) like mirror. FIG. 6 shows an example location of a mirror 23 on structure 10. Mirror 23 may, for example, be made with a deposition of alternating dielectric materials of a quarter-wave thickness. The alternating layers of materials may include Si and $SiO_2$ or some other high and low index materials. These materials may be deposited at the center area of a substrate or structure 10 on the side opposite of the side for an actuator.

Figure 2:
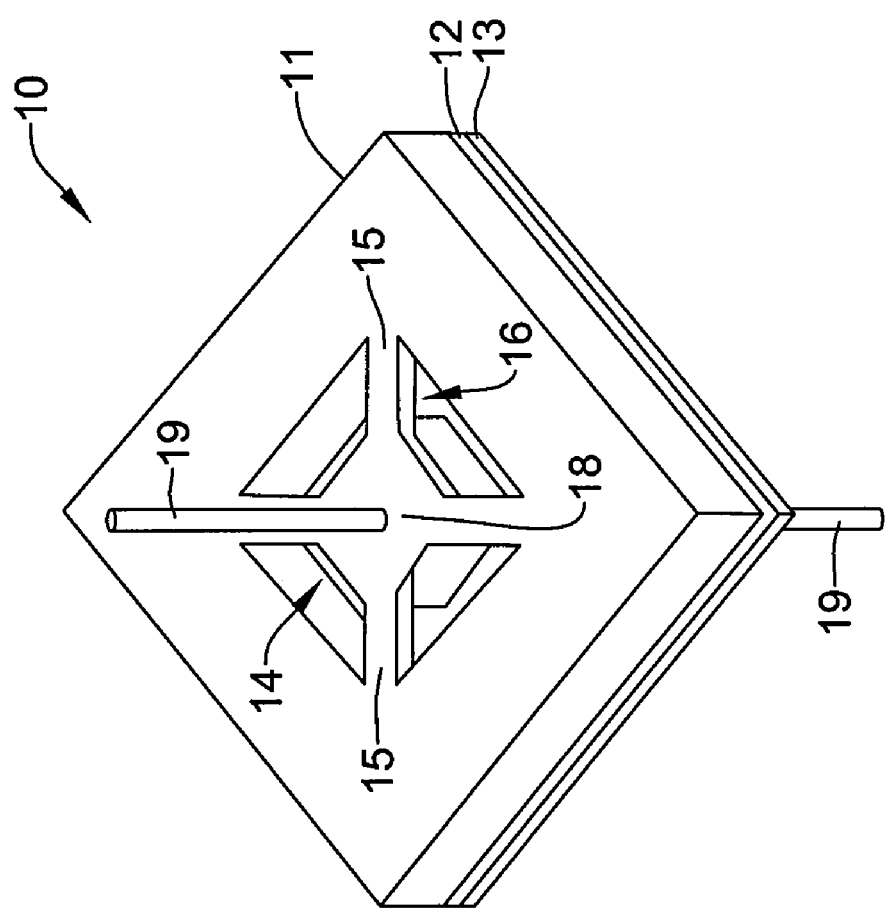
FIG. 2 is a diagram of a silicon structure that may permit an infrared light beam to pass through the structure because of the infrared transmittance of the silicon.

Structure 10 may be modeled after RLG mirrors with $SiO_2$ drilling. Short-wavelength infrared (SWIR) laser transmission through the silicon may be had, if desired, as shown by an infrared light 19 in FIG. 2. Often, the structure is not necessarily designed to permit light 19 to go through the transducer mirror structure 10. In some designs, there may be sufficient leakage of light 19 for monitoring purposes.

Use of silicon for structure 10 may lead to low cost fabrication. Another approach for making a structure 10 that may achieve the purpose of structure 10 may be a use of glass in lieu of silicon. To make and machine glass to achieve such a structure could be much more expensive to fabricate than the silicon structure 10. Significant savings may be achieved by making numerous structures 10 from silicon at a wafer level.

Figure 3:
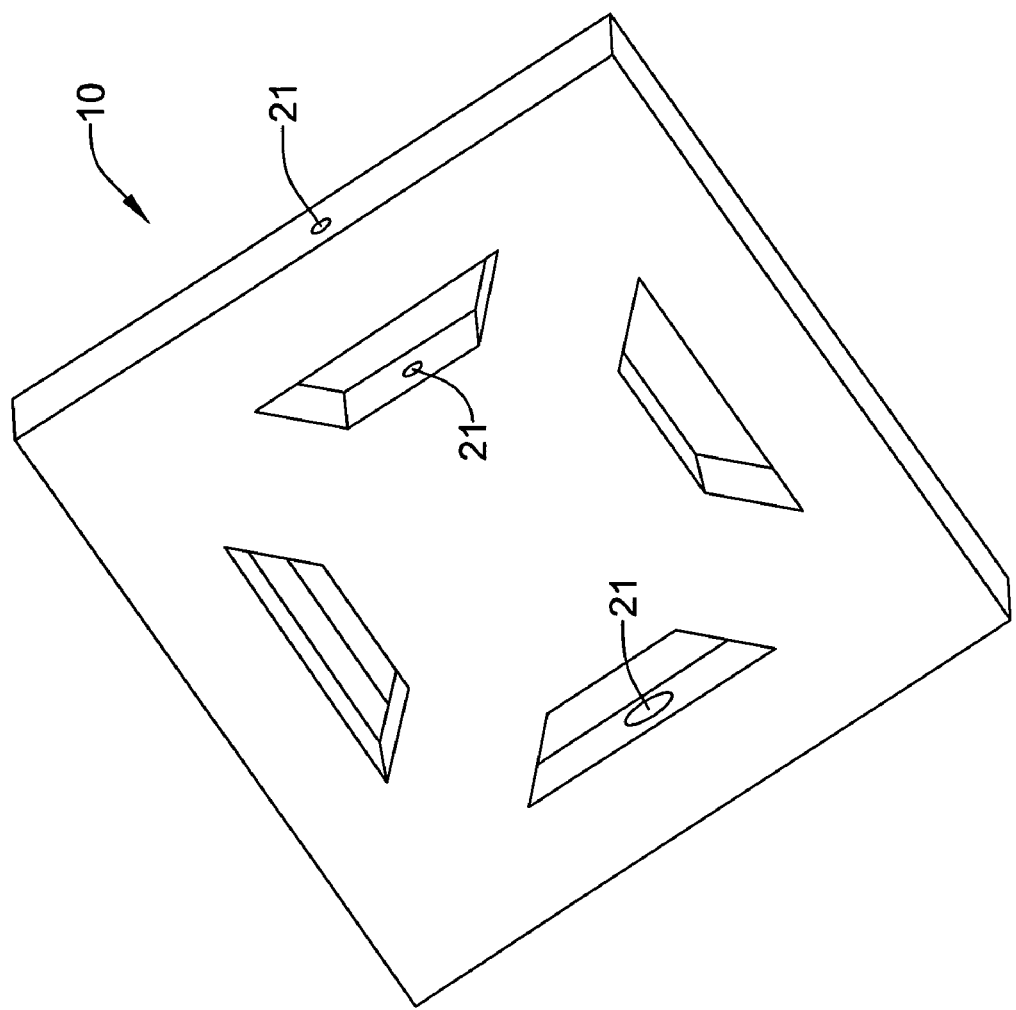
FIG. 3 is a diagram of a transducer mirror structure having a lateral hole for holding a driver or actuator in place with a side pin-like item.
Figure 4:
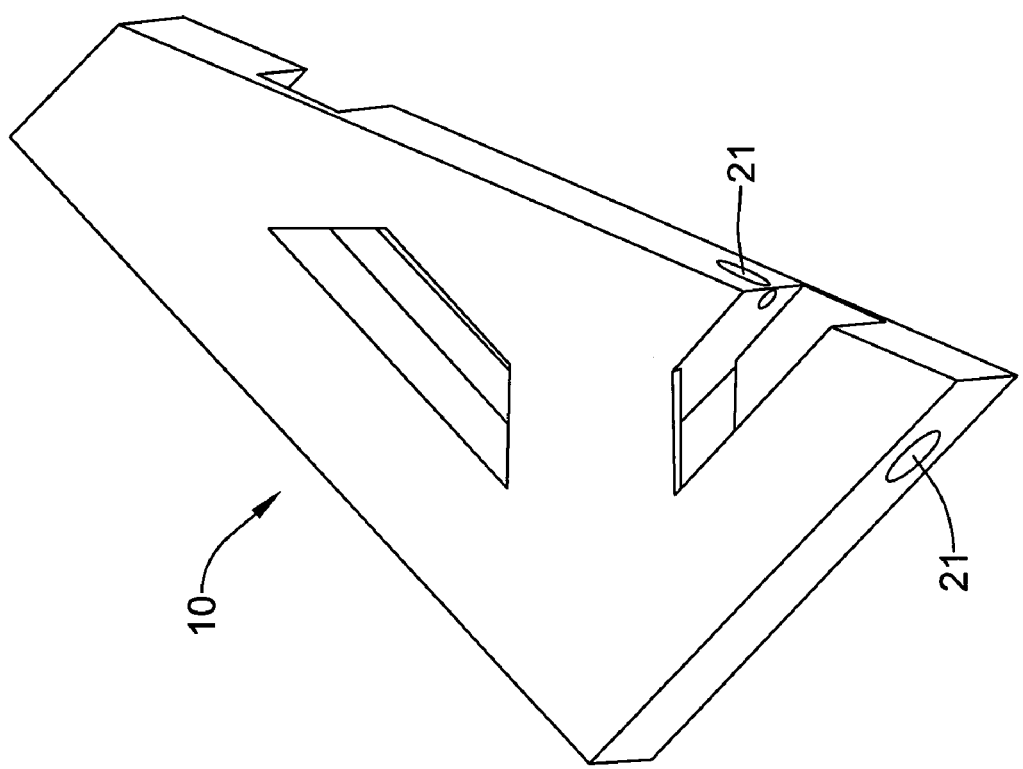
FIG. 4 is a cutaway diagram of the structure of FIG. 3.
Figure 8:
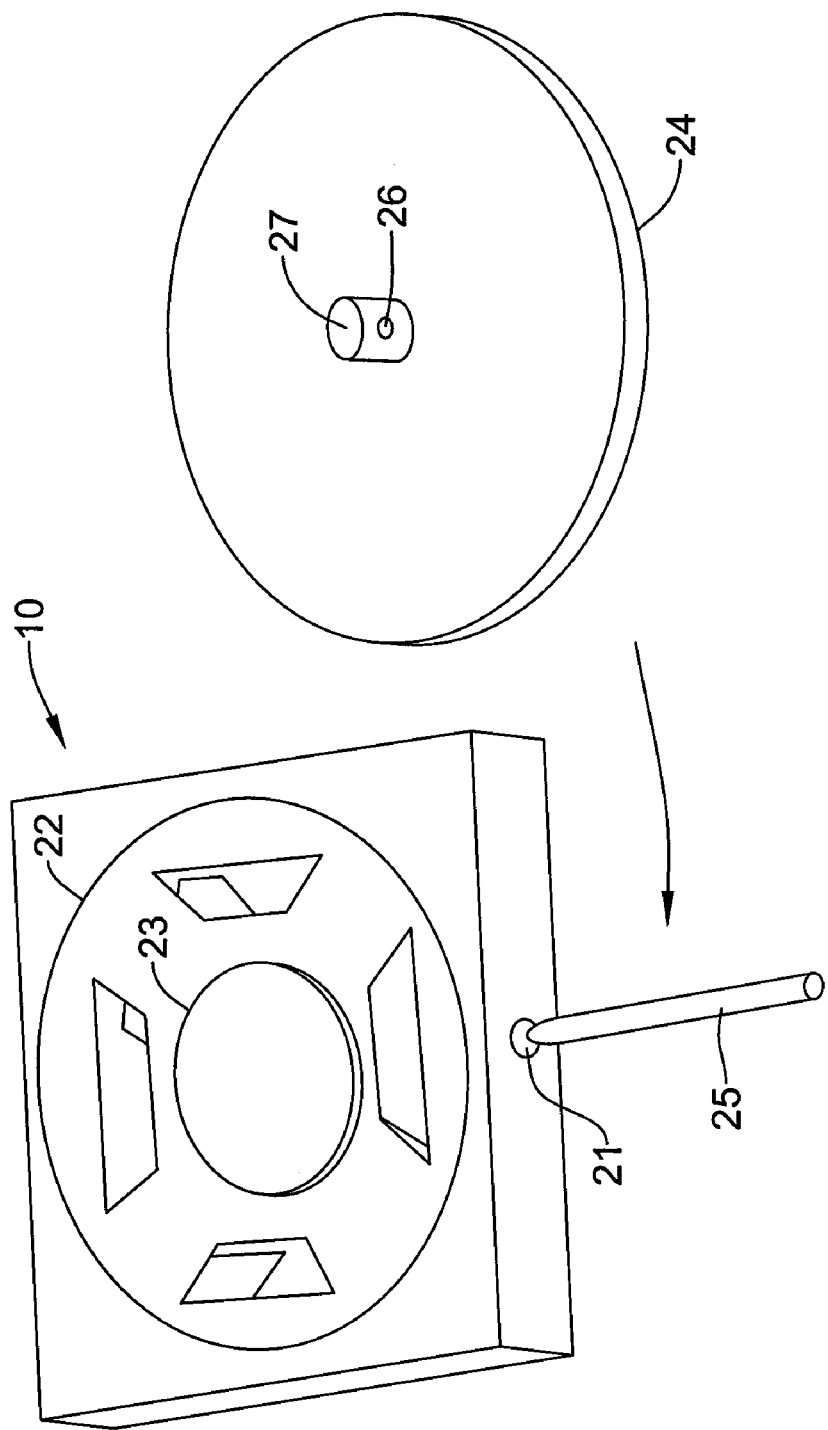
FIG. 8 is a diagram of the components for attaching the actuator to the transducer mirror structure.
Figure 9:
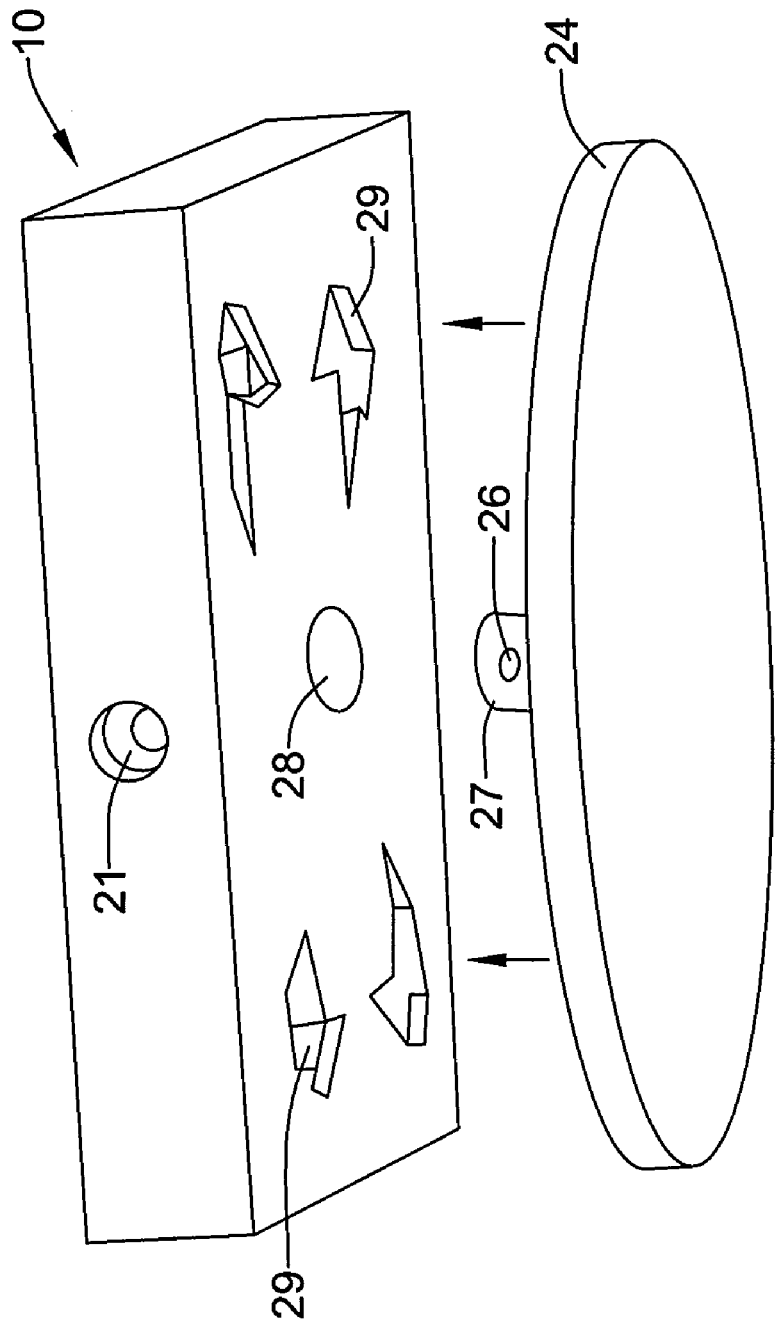
FIG. 9 is a diagram showing the position of the actuator for attachment to the transducer mirror structure.
Figure 10:
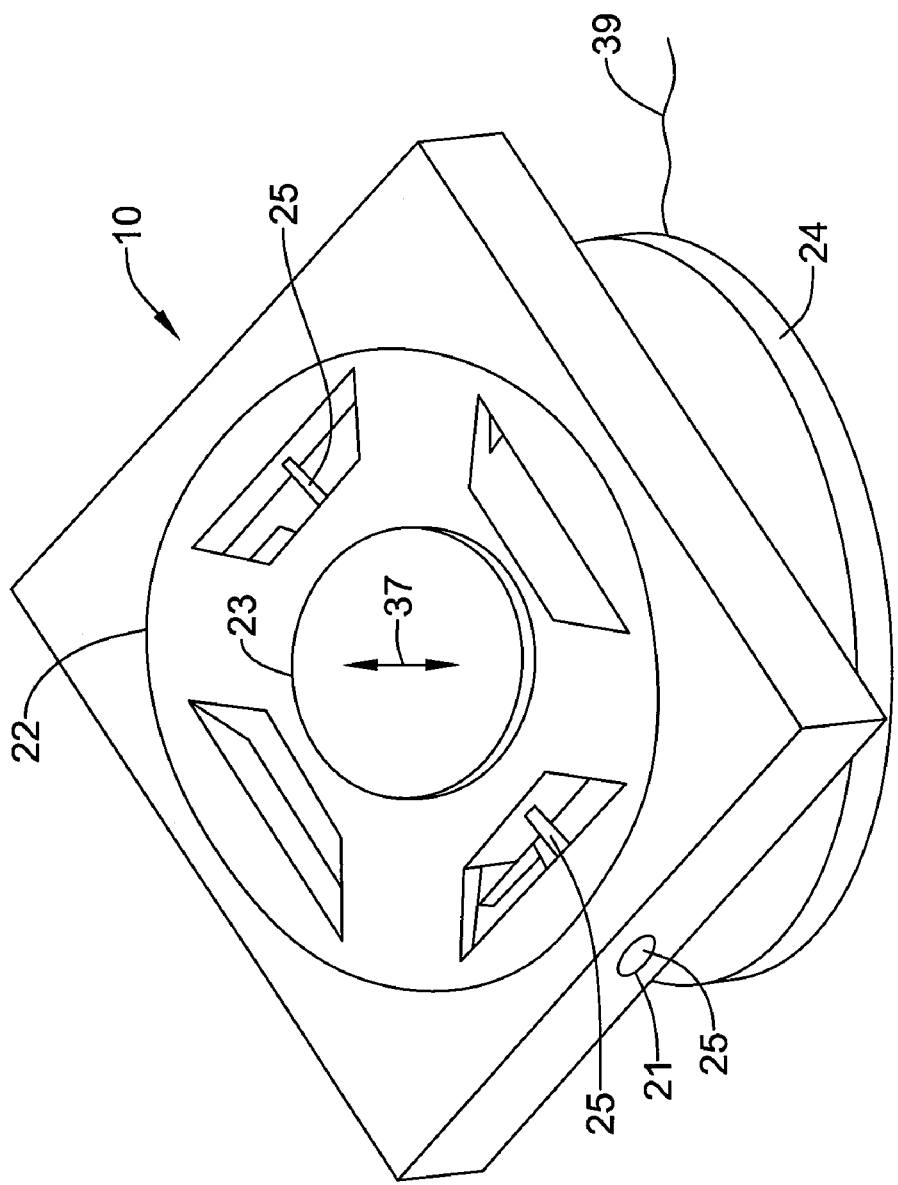
FIG. 10 is a diagram of the transducer mirror structure assembled with the seal, mirror and actuator.

FIG. 3 is a diagram which shows a version of structure 10 with a hole 21 for holding a piezo electric driver with a pin on the side of the structure. FIG. 4 is a cutaway diagram of the structure shown in FIG. 3. FIGS. 8-10, as described herein, show further information of this approach for securing an actuator or driver to a transducer mirror structure. Another approach without a side pin is shown in FIGS. 11 and 12.

Figure 5:
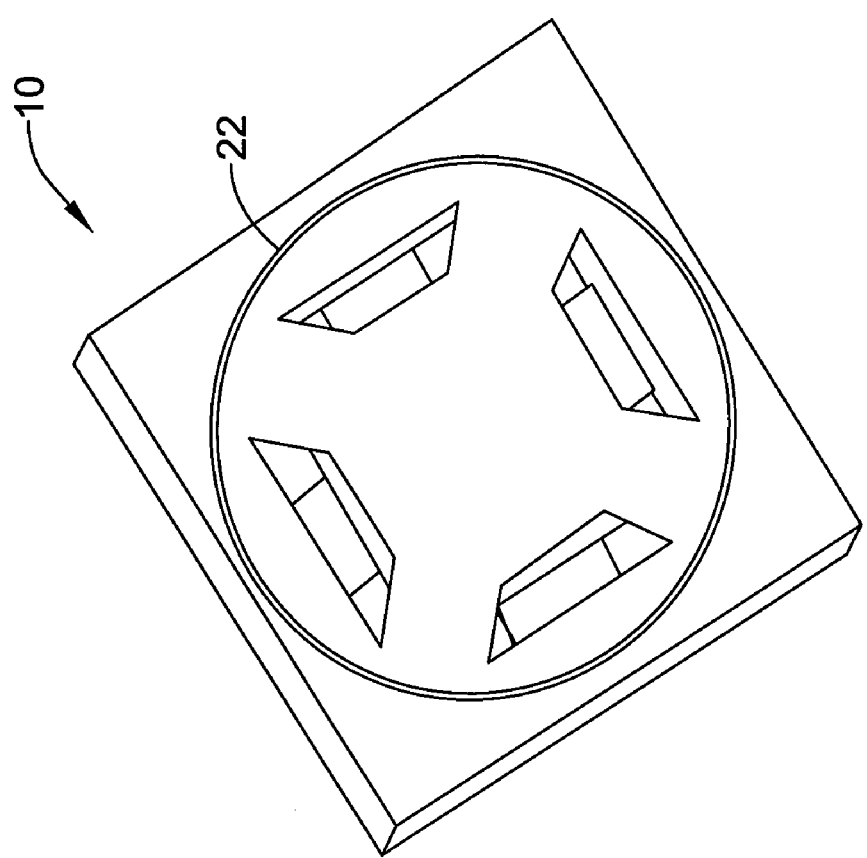
FIG. 5 is a diagram of the transducer mirror structure having a seal on the outer portion of the structure for hermetic containment relative to another structure such as a cavity.
Figure 7:
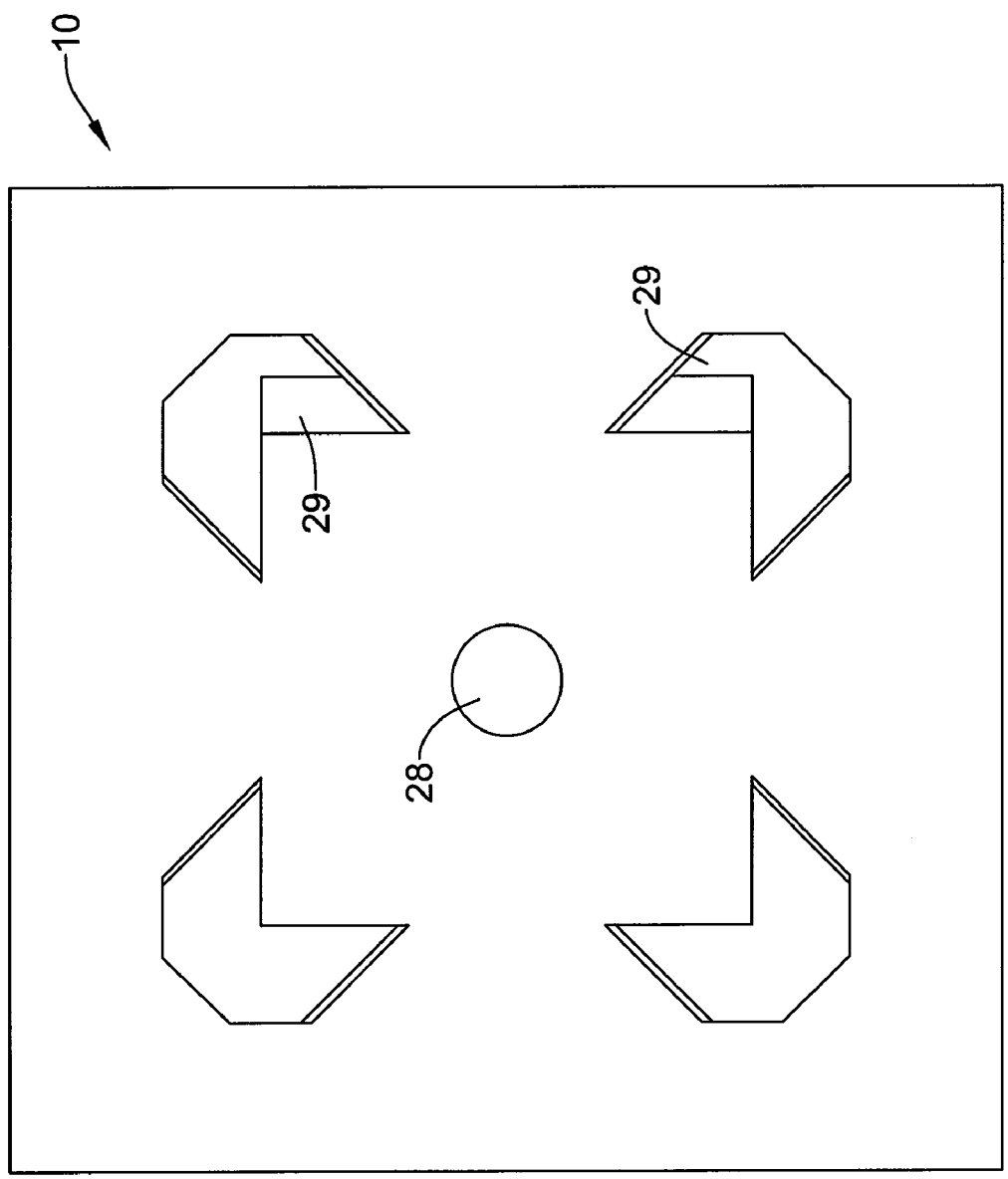
FIG. 7 is a diagram of the transducer mirror structure showing the actuator side, inner portion supports and a hole for securing an actuator.

FIG. 5 is a diagram of structure 10 shown with a seal 22 on the surface near an outer or peripheral portion so as to hermetically contain a mirror within another structure such as a cavity. The seal could, in some instances, be on the outside edge of structure 10. FIG. 6 is a diagram of structure 10 in FIG. 5 but additionally having a dielectric mirror 23 formed or deposited on the surface of the inner or center portion of structure 10. FIG. 7 is a diagram of structure 10 with gaps and resulting supports 29, e.g., legs, links, adapted or etched, and a hole 28 for attaching an actuator such as piezo electric driver on structure 10. FIG. 8 is a diagram of components for implementing an actuation mechanism for structure 10. Component 24 is an actuator such as, for example, a piezo electric driver. Component 25 is a pin or like item that may be placed in hole 21 of structure 10 and hole 26 of a shaft or pin 27 attached to the actuator or driver 24.

FIG. 9 is a diagram of the side of structure 10 upon where the actuator or driver 24 may be attached with short pin or shaft 27 inserted into a hole 28 of structure 10. Etched gaps with resulting thin supports 29 for center portion of structure 10 are shown on the actuator side. FIG. 10 is a diagram of the mirror side of structure 10 with the actuator or driver 24 attached to structure 10 and held in with pin 25 inserted through hole 21 of structure 10 and hole 26 of pin or shaft 27 of actuator or driver 24. Glue may be applied to pin 25 and/or hole 21 for sealing to prevent gas from escaping from the cavity through any portions of hole 21. An indication 37 may show a direction of mirror 23 motion relative to the perimeter of structure 10 such as at the seal 22. Line 39 may provide control of actuator 24 which is for providing the motion according to indication 37 to mirror 23. The motion of mirror 23 may be for adjustment of mirror position.

Figure 11:
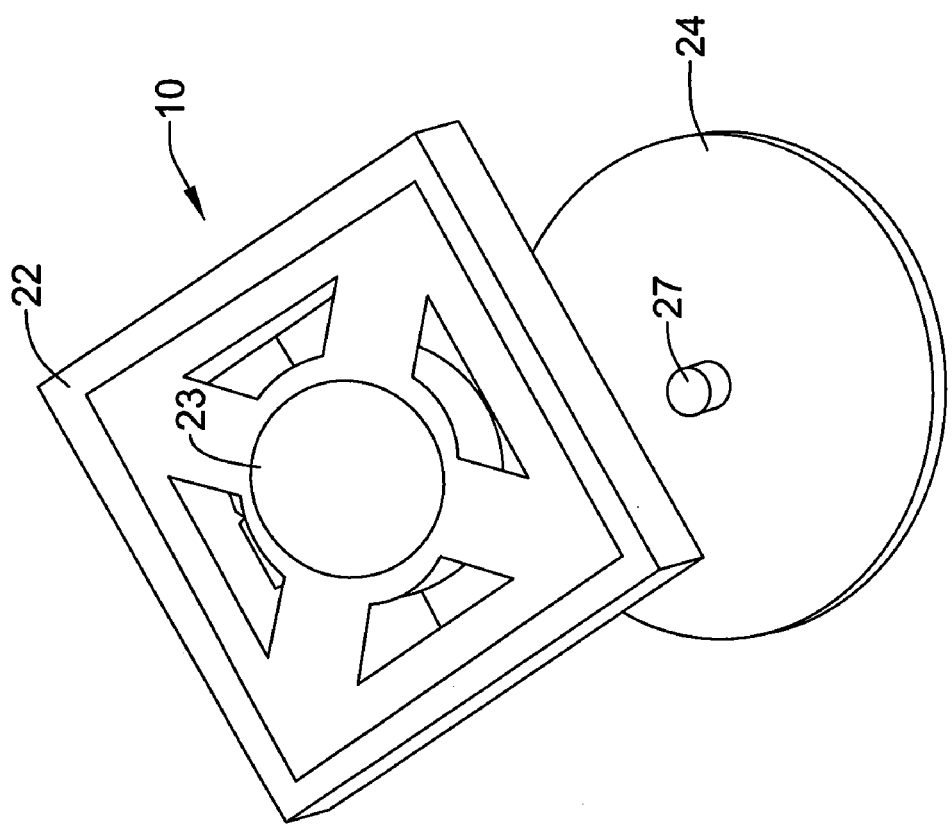
FIG. 11 is a diagram with a mirror end view of the transducer mirror structure and actuator which are attachable to each other without a side pin-like item to hold the actuator in place relative to the transducer mirror structure.
Figure 12:
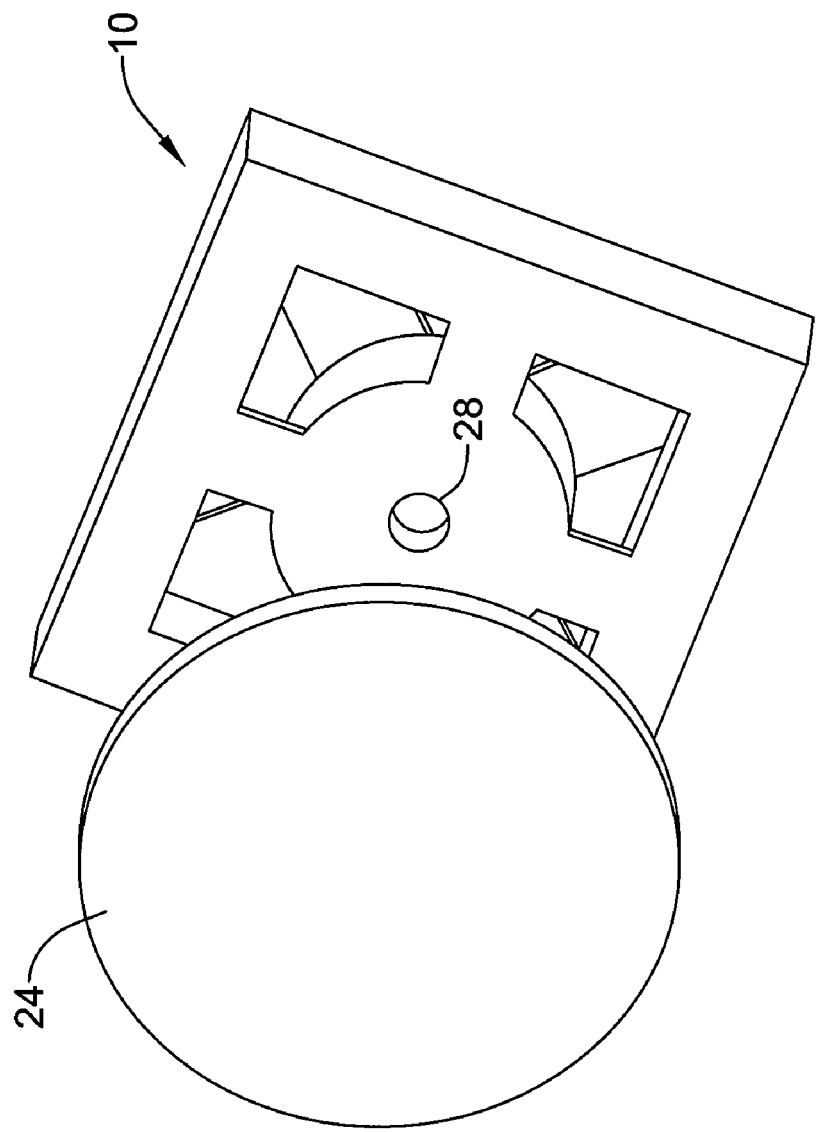
FIG. 12 is a diagram with actuator end view of the structure of FIG. 11.

FIG. 11 is a diagram with a mirror end view of the transducer mirror structure 10 and driver or actuator 24, such as a piezo electric driver, which are attachable to each other without a side pin-like item 25 like that in FIG. 10, to hold the actuator 24 in place relative to the transducer mirror structure 10. FIG. 12 is a diagram with actuator 24 end view of the structure of FIG. 11. The main attachment may be the pin or shaft 27 in FIG. 11 on the actuator 24 being glued to the back of the silicon transducer mirror structure 10, where pin or shaft 27 fit into hole 28 in structure 10 as shown in FIG. 12. Actuator 24 may be sealed to the backside of structure 10 so that any gas would not escape from the cavity through the structure 10 openings. The front side of the cavity may be sealed to the structure around the periphery. The external perimeter of structure 10 might be circular rather than a square cut. Hole 28 may be etched in the silicon structure 10 at the same time that the other openings are made in the structure.

Figure 13:
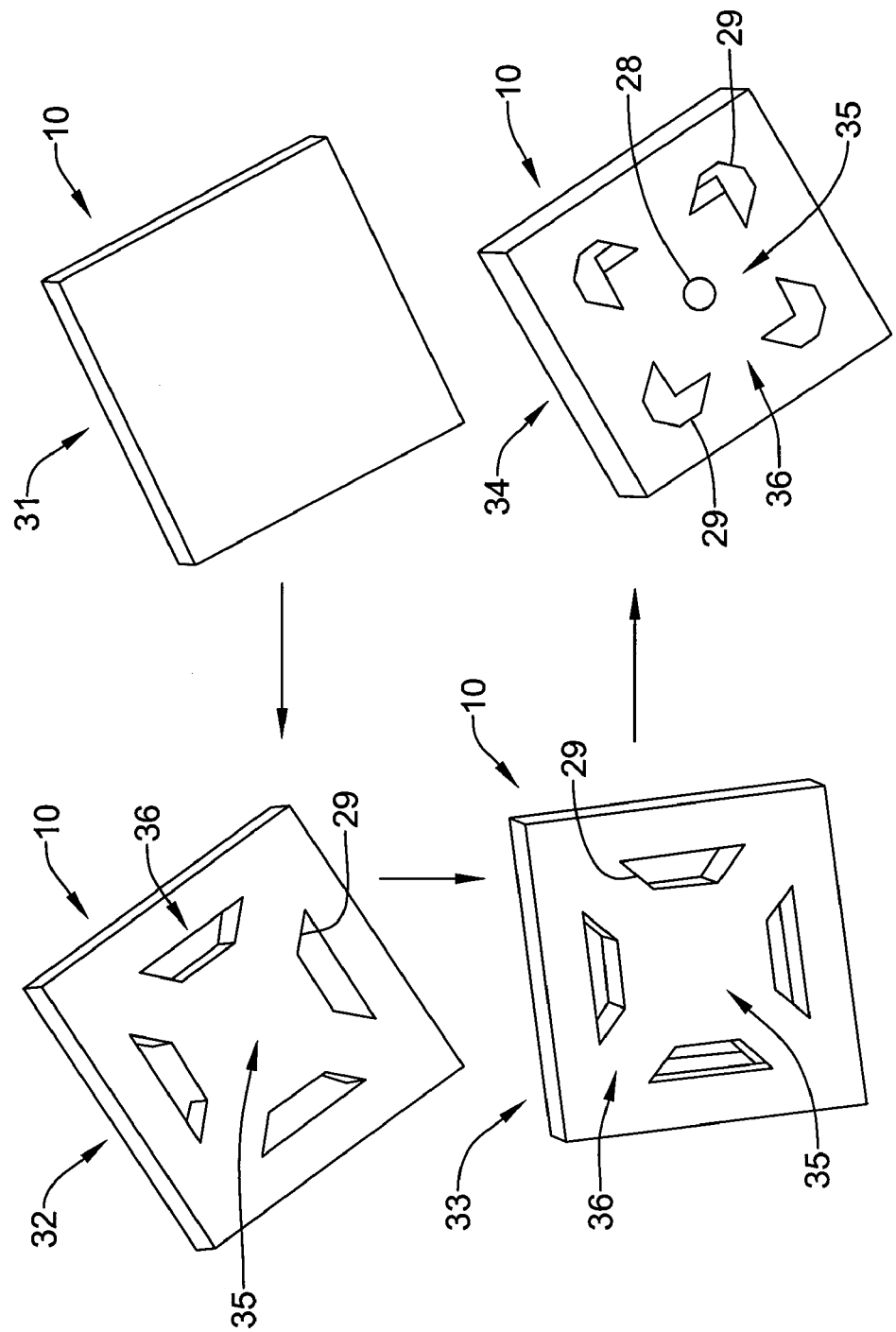
FIG. 13 is a flow diagram of a fabrication process of the transducer mirror structure.

FIG. 13 is a flow diagram of a fabrication process of the transducer structure 10. Step 31 may be obtaining a silicon piece, block or substrate for structure 10 which may be etched to form gaps, slots, links, legs or supports 29 to hold a center portion 35 relative to an outer portion 36. Step 32 may include a straight RIE etch for making, for instance, gaps for the flexible supports 29. Step 33 may include a second etch which is a KOH under etch for further making the supports 29. Step 34 may include making a hole 28 for holding an actuator. Gaps, slots, links, legs and supports 29, and the like, may be of various shapes. Other steps may include adding a mirror 23 and a seal 22 as described herein, and attaching resultant structure 10 to another structure 38 shown in FIG. 14, such as a cavity of a cavity ring-down spectroscopy system.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A silicon mirror assembly comprising:
   a silicon piece comprising:
      a perimeter section;
      a center section moveable relative to the perimeter section;
      a mirror for reflecting light in a cavity disposed on a first surface of the center section;
      a web of two or more connections situated between the center section and the perimeter section and coupling the center section to the perimeter section; and
      a piezoelectric driver having an upper surface, the piezoelectric driver comprising a cylindrical shaft extending in an upward direction away from the upper surface of the piezoelectric driver, the cylindrical shaft including a hole, the piezoelectric driver coupled to the perimeter section by a pin inserted through both a hole provided in an outer wall of the perimeter section and the hole provided in the shaft such that the pin extends from a location outside of the outer wall of the perimeter section and through both the outer wall of the perimeter section and the cylindrical shaft, the cylindrical shaft coupled to the perimeter section for moving the center section including the mirror relative to the perimeter section.

2. The assembly of claim 1, further comprising a silicon oxide layer between the first surface of the center section and the mirror.

3. The assembly of claim 2, further comprising a silicon layer between the silicon oxide layer and the mirror.

4. The assembly of claim 2, wherein:
   the web of two or more connections is formed by etching gaps from a second surface of the piece of silicon to the silicon oxide layer; and
   the web of two or more connections is further formed by etching under the second surface of the connections.

5. The assembly of claim 1, further comprising:
   a seal disposed around a periphery of the perimeter section proximate the mirror wherein,
   the seal is for attaining a hermetic sealing of the mirror within the cavity.

6. A method for making a transducer mirror assembly comprising:
   providing a substrate comprising silicon;
   forming a layer of oxide on a first surface of the substrate;
   etching the substrate from a second surface of the substrate to the oxide layer to form a web of two or more legs for providing a flexible structure between a center section and an outside section of the substrate;
   forming a hole in the outside section of the substrate;
   forming a thin layer comprising silicon on the layer of oxide;
   forming a mirror on the thin layer; and
   inserting a pin through the hole provided in the outside section of the substrate and through a hole provided in a cylindrical shaft of a piezoelectric driver to couple the piezoelectric driver to the outside section of the substrate such that the pin extends from a location exterior to the outside section of the substrate and through both the outside section of the substrate and the cylindrical shaft, wherein the piezoelectric driver is adapted to move the center section relative to the outside section.

7. The method of claim 6, wherein:
   exerting a force on the second surface at the center section moves the mirror relative to the outside section; and
   the mirror moves in line with an axis.

8. The method of claim 7, wherein infrared light can propagate through the thin layer, the oxide layer and the substrate, in either direction.

* * * * *